United States Patent
Spartiotis et al.

(10) Patent No.: US 6,797,960 B1
(45) Date of Patent: Sep. 28, 2004

(54) SELF TRIGGERED IMAGING DEVICE FOR IMAGING RADIATION

(75) Inventors: Konstantinos Evangelos Spartiotis, Espoo (FI); Stefan Jurthe, Espoo (FI); Jouni Pyythiä, Espoo (FI)

(73) Assignee: Simage Oy, Espoo (FI)

(*) Notice: Subject to any disclaimer, the term of this patent is extended or adjusted under 35 U.S.C. 154(b) by 0 days.

(21) Appl. No.: 09/937,483
(22) PCT Filed: Apr. 26, 2000
(86) PCT No.: PCT/IB00/00581
§ 371 (c)(1), (2), (4) Date: Nov. 27, 2001
(87) PCT Pub. No.: WO00/65825
PCT Pub. Date: Nov. 2, 2000

(30) Foreign Application Priority Data

Apr. 26, 1999 (GB) .............................. 9909572
Jul. 13, 1999 (GB) .............................. 9916407

(51) Int. Cl.[7] ................................................ G01T 1/16
(52) U.S. Cl. .............................. 250/370.09; 250/370.01
(58) Field of Search ....................... 250/370.01, 370.07, 250/370.08, 370.09, 370.12, 370.13, 370.14, 371

(56) References Cited

U.S. PATENT DOCUMENTS 5,513,252 A   4/1996   Blaschka et al.
5,786,597 A * 7/1998  Lingren et al. ........ 250/370.09

FOREIGN PATENT DOCUMENTS

| EP | A 0287197 | 10/1988 |
| EP | A 0571135 | 11/1993 |
| EP | 0756416 A1 | 1/1997 |
| GB | 2 304 017 | 3/1997 |
| GB | 2 319 394 | 5/1998 |
| GB | 2 335 540 | 9/1999 |
| WO | WO95/33332 | 12/1995 |

OTHER PUBLICATIONS

Puertolas D et al.: An ISPA–camera for gamma rays; 1994 Nuclear Science Symposium and Medical Imaging Conference, NSS/MIC, vol. 42, No. 6, pt. 2, pp. 2221–2228, IEEE Transactions on Nuclear Science, Dec. 1995, IEEE, USA.

* cited by examiner

Primary Examiner—Constantine Hannaher
Assistant Examiner—Timothy Moran
(74) Attorney, Agent, or Firm—Kenyon & Kenyon

(57) ABSTRACT

A semiconductor radiation imaging assembly comprises a semiconductor imaging device including at least one image element detector. The imaging device is arranged to receive a bias for forming the at least one image element detector. The assembly also includes bias monitoring means for monitoring the bias for determining radiation incident on the image element detector. Preferably, the imaging device comprises a plurality of image element detectors the bias for at least some of which is monitored for determining incident radiation. More preferably, the bias for all the detector elements is monitored.

52 Claims, 17 Drawing Sheets

DIFFERENTIAL (EDGE) DETECTION

BLOCK DIAGRAM OF A DOSE DETECTION TRIGGER

BLOCK DIAGRAM OF A SECOND DOSE DETECTION TRIGGER

BIAS CURRENT MANAGEMENT

2nd ORDER HIGH PASS FILTER
(FOR LOW PASS
INTERCHANGE R AND C)

COMPARATOR INCL.
HOLD/RESET AND
VISUALISATION

Plot 1

Plot 4

4mm AL    100 / 1000 Hz

Plot 7

Plot 8

Plot 9

SELF TRIGGERED IMAGING DEVICE FOR IMAGING RADIATION

This invention relates to a self-triggering imaging assembly for imaging radiation and to a self-triggerable imaging system.

BACKGROUND OF THE INVENTION

Imaging devices comprising an array of image elements of various types are known Charged coupled image sensors (also known as charged coupled devices (CCDs)) form one type of known imaging device. A CCD type device operates in the following way:
1. Charge is accumulated within a depletion region created by an applied voltage. For each pixel (image cell) The depletion region has a potential well shape and constrains electrons under an electrode gate to remain within the semiconductor substrate.
2. Voltage is applied as a pulse to the electrode gates of the CCD device to clock each charge package to an adjacent pixel cell. The charge remains inside the semiconductor substrate and is clocked through, pixel by pixel, to a common output.

During this process, additional charge cannot be accumulated.

Another type of imaging device which is known is a semiconductor pixel detector which comprises a semiconductor substrate with electrodes which apply depletion voltage to each pixel position and define a charge collection volume. Typically, simple buffer circuit read out the electric signals when a photon is photo-absorbed or when ionising radiation crosses the depletion zone of the substrate. Accordingly pixel detectors of this type typically operate in a pulse mode, the numbers of hits being accumulated externally to the imaging device. The buffer circuits can either be on the same substrate (EP-A-0,287,197) as the charge collection volumes, or on a separate substrate (EP-A-0,571,135) that is mechanically bonded to a substrate having the charge collection volumes in accordance with, for example, the well known bump-bonding technique.

A further type of device is described in International application WO95/33332. In WO95/33332, an Active-pixel Semiconductor Imaging Device (ASID) is described. The ASID comprises an array of image elements including a semiconductor substrate having an array of image element detectors and a further array of image element circuits. The image element detectors generate charge in response to instant radiation. Each image element circuit is associated with a respective image element detector and accumulates charge resulting from radiation incident on the image element detector. The image element circuits are individually addressable and comprise circuitry which enables charge to be accumulated from a plurality of successive radiation hits on the respective image element detectors. The device operates by accumulating charge on the gate, for example, of a transistor. Accordingly, analogue storage of the charge value is obtained. At a determined time, the charge from the image element circuits can be read out and used to generate an image based on the analogue charge values stored in each of the image element circuits.

CCD devices suffer from disadvantages of limited dynamic range, due to the limited capacity of the potential well inside the semiconductor substrate, and also to the inactive times during which an image is read out. Pulse counting semiconductive pixel devices also have the disadvantage of limited dynamic range. As these devices read the pixel contact when a hit is detected, they suffer from saturation problems at high counting rates. The semiconductor image element device according to WO95/33332 provides significant advantages over the earlier prior art by providing a large dynamic range for the accumulation of images.

It has been proposed to utilise the above-mentioned CCD and semiconductor devices to replace the film used in conventional radiation imaging systems, in order to provide real-time imaging and a more controlled lower dosage of radiation for a given exposure.

In a known arrangement, a CCD is electrically connected to an X-ray source. When the X-ray source is energised a start signal is transmitted alone the connecting wire to the CCD and its control circuitry to begin image acquisition and read-out.

In a optional arrangement disclosed in U.S. Pat. No. 5,513,252 there is no connection to the X-ray source. Instead, the CCD is continually read-out prior to radiation. A signal derived from the CCD is compared with a reference level. If the signal exceeds the reference level, the image acquisition of the CCD is initiated, that is to say the CCD stops being read out and the image starts to accumulate on the CCD.

European Patent Application Publication No. 0 756 416 A1 discloses a CCD used as an imaging device in which charge accumtulated in the CCD elements is clocked from several rows into a register in order to sum the charges. The summed result is put to a threshold test. Onset of X-ray radiation is detected when the signal applied to the threshold test exceeds a reference level. Image acquisition is then initiated, as described above i.e. only then will the CCD start accumulating the image.

In yet another arrangement the X-ray source and CCD have again no physical connection. A further sensor is arranged close to the imaging array for the CCD to detect the onset of X-ray radiation. On detection of incident X-ray energy, the sensor sends a signal to the CCD control circuitry to initiate image acquisition, as before.

The foregoing prior art systems involve a delay between activation of the radiation source and initiation of image acquisition. Since in radiation imaging, in particular X-ray imaging, the exposure to irradiation and radiation devices should be kept as low as possible it is desirable to reduce the delay as much as possible. Furthermore, the CCD approach is unsuitable for determining an end of an exposure. An additional sensor or a connection to the radiation source is necessary to provide an exposure trigger indicating end of irradiation.

SUMMARY OF THE INVENTION

In accordance with an embodiment according to a first aspect of the invention there is provided a semiconductor radiation imaging assembly, comprising: a semiconductor imaging device including at least one image element detector, said imaging device arranged to receive a bias for forming said image element detector; and bias monitoring means for monitoring said bias for determining radiation incident on said image element detector.

In accordance with an embodiment according to a second aspect of the invention, there is provided a method for providing a semiconductor imaging assembly, including an image element detector, comprising: monitoring a bias for said image element detector to determine radiation incident on said image element detector; and initiating a trigger for said bias fulfilling a predetermined condition.

In accordance with an embodiment according to a third aspect of the invention, there is provided a self-triggerable semiconductor radiation imaging system, comprising: a semiconductor imaging assembly as or operable as described in the foregoing paragraphs; control electronics coupled to said imaging assembly for receiving signals, including trigger signals, therefrom; signal storage means for storing signals coupled from said control electronics; an image processor for processing signals coupled from said control electronics; and a display unit for displaying images provided by said image processor.

Embodiments in accordance with the first, second or third aspects of the invention advantageously provide a substantially instantaneous or real-time response to radiation incident on an or a plurality of image element detectors by monitoring the bias applied to form the image element detector/s. Such embodiments may provide trigger signals in direct response to radiation incident on the image element detector/s, yet by indirect monitoring of the incident radiation, thereby obviating the need for reading out data from the image elements. Further, the embodiments provide for self-triggering image detector devices and systems, and obviate the need for trigger signals to be provided from X-ray sources to the control electronics of such systems for identifying beginning and/or ending of exposure.

Furthermore, since the bias represents an average of the radiation incident over the whole area of an array of image elements it provides a robust indication of the total radiation incident over that area, and provides a sensitive self-triggering mechanism.

Suitably, the semiconductor imaging device comprises a semiconductor substrate supporting a first and second conductive layer on respective first and second surfaces. The first and second conductive layers at least partially oppose each other for applying the bias between them to form a radiation detection zone for the image element detector.

Typically, the first conductive layer comprises a substantially continuous layer across the first substrate surface, and the second conductive layer comprises a plurality of image element electrodes for defining respective radiation detection zones for a plurality of image element detectors.

Advantageously, the bias monitoring means is adapted to provide a trigger for the bias fulfilling a predetermined criterion.

In accordance with a first preferred embodiment, the bias monitoring means determines a rate or direction of change of the bias, and more preferably discriminates between different rates or direction of change. Thus, increases and decreases in bias due to corresponding increases and decreases in incident radiation intensity may be determined and utilised to initiate suitable trigger signals.

Preferably, one or more threshold values are set corresponding to bias levels representative of incident radiation levels at start of exposure and/or end of exposure of which triggers are to be initiated. Such triggers are initiated for the bias transgressing respective bias levels at and/or in an appropriate direction.

The bias monitoring means preferably monitors the bias current, and provides a signal representative of the bias current, although for an assembly having the bias supplied from a non-constant output voltage supply the bias voltage may be monitored. This representative signal is differentiated, the resulting signal low-pass filtered (by an integrator for example) and the filter result input to a comparator for comparing with one or more threshold levels. Thus, typically the threshold levels are compared against a value of an intermediate signal representing the incident radiation and derived from the bias current.

An example of a suitable differentiator is a high pass filter, and an example of a suitable low pass filter is an integrator. Cut-off frequencies for the high pass filter differentiator and the low pass filter integrator suitably lie in the ranges 10–200 Hz. and 500 Hz.–2 kHz. respectively.

In accordance with a second preferred embodiment of the invention, the bias monitoring means accumulates a bias value which represent aggregate radiation incident on the image element detector/s, which advantageously offers improved radiation detection rejection against reliability. Thus, the likelihood of false positive triggers is reduced without adversely affecting the sensitivity to incident radiation.

Preferably, an image element dark or quiescent bias value is subtracted from a value representing the bias, and the resulting signal is then integrated to provide an indication of the total accumulated bias value after correction for the quiescent bias value. One or more threshold levels arc set against which the accumulated bias value is compared, to initiate suitable trigger signals such as start of and/or end of exposure trigger signals. Preferably, for an imaging device comprising more than one image element detector, then a dark or quiescent bias value corresponding to all of the individual image elements is subtracted from the value representing the bias value.

Suitably, sample and hold circuitry is configured to record the bias value prior to a radiation exposure in order to obtain a suitable quiescent bias value.

In accordance with a third preferred embodiment of the invention, an integrated signal representative of the bias, preferably bias current but optionally voltage, is subtracted from the signal representative of the bias to derive a signal corresponding to the radiation incident on the image element detector/s. The resulting signal is then compared with threshold values to initiate suitable trigger signals.

BRIEF DESCRIPTION OF THE DRAWINGS

Embodiments of the invention will now be described, by way of example only, with reference to the accompanying drawings in which like elements have like reference signs and in which.

DETAILED DESCRIPTION OF THE PREFERRED EMBODIMENTS

Figure 1:
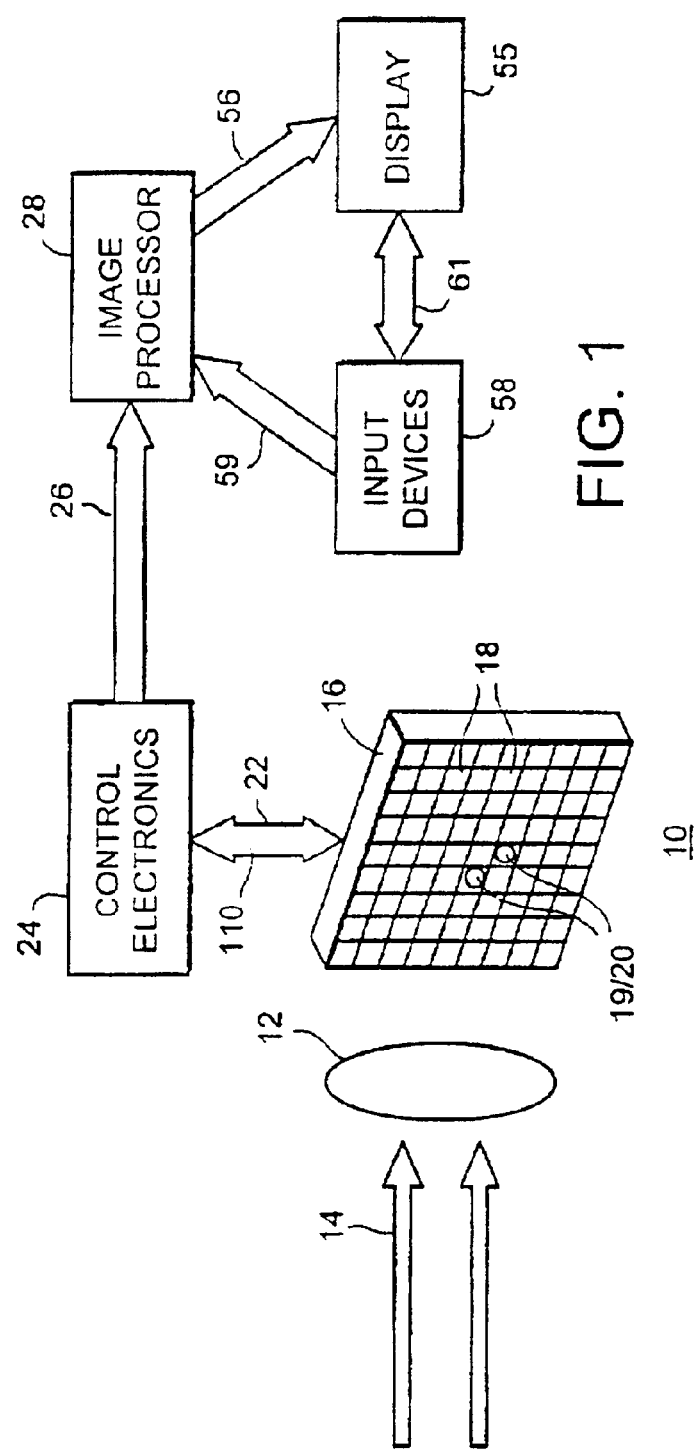
FIG. 1 is a schematic block diagram of an overall imaging configuration.

FIG. 1 is a schematic block diagram of an example of an imaging system suitable for use with the present invention. This particular embodiment is directed to the imaging of high energy radiation, for example X-ray radiation. By high energy radiation is meant radiation having an energy in excess of approximately 1 KeV. However, the invention is by no means limited to high energy radiation such as X-rays but could be applied to the detection of any particular radiation, for example γ-ray, β-ray, α-ray, infra-red or optical radiation, subject to an appropriate choice of semiconductor substrate.

The imaging system 10 of FIG. 1 is shown to provide imaging of an object 12 subject to radiation 14. In this example the radiation may, for example, be X-ray radiation as mentioned above, but could alternatively be γ-ray, β-ray or α-ray radiation. The object 12 may, for example, be part of a human body. The imaging device 16 comprises a plurality of image elements (here elements 18 of a two dimensional image element array). In the following, reference will be made to image elements 18, although it will be appreciated that in other embodiments the individual image elements may have a configuration other than that of an element within a two dimensional array (eg a strip arrangement).

Control electronics 24 includes processing and control circuit for controlling the operation of the imaging device, or an array of imaging devices. The control electronics 24 is interfaced to the imaging device 16 via path 22 and enables the readout circuits 20 associated with individual image elements 18 to be addressed (e.g. scanned) for reading out charge from the readout circuits 20 at the individual image elements 18. The charge readout is supplied to Analog-to-Digital Converters (ADCS) for dicitisation and Data Reduction Processors (DRPs) for processing the digital signal. A bias 110 for the imaging device may also be applied over interface 22. Optionally, the bias may be applied via some other path.

The control electronics 24 is further interfaced via a path represented schematically by the arrow 26 to an image processor 28. The image processor 28 includes data storage in which it stores digital values representative of the charge values read from each image element along with the position of the image element 18 concerned. The image processor 28 builds tip an image for display The data storage can store digital values for up to two image frames, i.e. signals corresponding to two images. Later signals overwrite or force out in a first in first out manner previously stored signals. A trigger signal determines where in the data storage the first signal for an exposure is located, and starts the read out of data from this location and then reads out the next n−1 data storage locations corresponding to the remaining n−1 image elements of an n element imaging system. For a start of exposure trigger, the first read out storage location corresponds to the start of exposure trigger. For an end of exposure trigger the image processor works back from the storage location corresponding to the trigger signal, to read out the remaining image frame signals corresponding to the radiation exposure. The values are read out by the image processor 28 to cause a representation of the data to be displayed on a display 55 via a path represented schematically by the arrow 56. The data can, of course, be printed rather than, or in addition to, being displayed and can be subjected to further processing operations, including non-volatile storage in magnetic media for example. Input devices 58, for example, a keyboard and/or other typical computer input devices, are provided for controlling the image processor 28 and the display 55 as represented by the arrows 59 and 61.

The imaging device detects directly high energy incident radiation and accumulates at each image element, a count of the incident radiation hits at that image element.

The imaging device can be configured as a single semiconductor substrate (eg, of silicon) with each image element comprising an image element detector 19 and image element circuitry 20. Alternatively, the imaging device 16 can be configured on two substrates, one with an array of image element detectors and one with an array of corresponding image element circuits 20, the substrates being mechanically connected to each other by, for example, conventional bump-bonding technology or any other appropriate technology.

Figure 2:
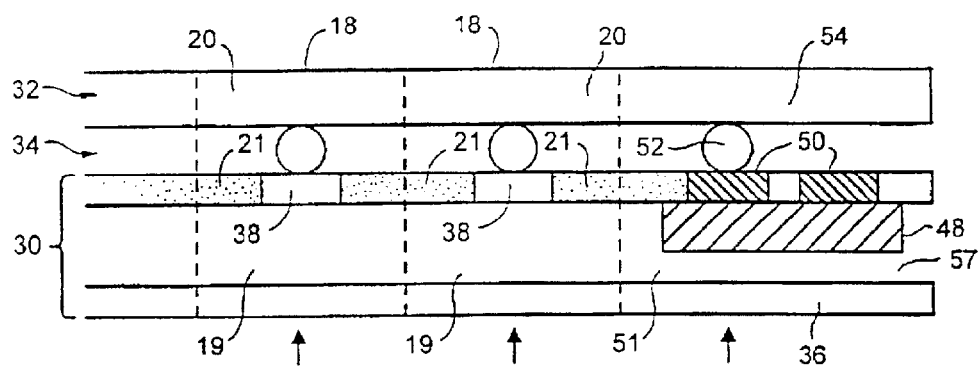
FIG. 2 is a cross-section of one example of an imaging device.

FIG. 2 is a schematic cross section of part of an imaging device 16. In this example, the imaging device 16 comprises an image detector substrate 30 connected to an image circuit substrate 32 by means of bump-bonds 34. An image element detector 19 of each image clement 18 is defined on the detector substrate 30 by a continuous electrode 36 which applies a biasing voltage and image element location electrodes 38, which collect charge, to define a detection zone for the image element 18. Such a detection zone comprises a charge generation volume in which charge is generated responsive to incident radiation, and caused to drift to respective electrodes under the influence of the bias. Preferably, a passivation material 21 such as aluminium nitride, silicon nitride or silicon oxide for example, is disposed between adjacent image element electrodes 38. Corresponding image element circuits 20 on the image circuit substrate 32 are defined at locations corresponding to the electrodes 38 (ie to the image element detectors 19). The image element circuits 20 are electrically connected to the corresponding electrodes 38 by bump-bonds 34. In this manner, when charge is generated in an image element detector 19 in response to incident radiation, this charge is passed via the bump-bond 34 to the corresponding image element circuit 20.

A continuous electrode 36 may be fabricated from suitably conductive material such as aluminium, gold, indium/platinum alloy or platinum/gold alloy, for example. The image element electrodes may be fabricated from a conductive material such as gold, platinum/gold alloy or nickel/gold alloy, for example.

Each image element 18 of the imaging device 16 is in effect defined on the substrate by electrodes 38 which apply a biasing voltage in cooperation with continuous electrodes 36 to define a detection zone (i.e. the image element detector 19) for the image element 18. Corresponding readout circuits on the readout substrate can comprise, for example, active image element circuits 20 as described in the aforementioned WO 95/33332. The image element detectors 19 are formed with a detection zone such that, when a photon is photo-absorbed in the semiconductor substrate 30 at an image element 18 creating an electric charge or when a charged radiation ionises the detection zone of the semiconductor substrate 30 at an image element 18, an electric pulse flows from the semiconductor detection zone to the readout circuit 20 for that image element 18 through the solder bump 34 for that image clement.

The actual size of the image element circuit and the image element detector will depend on the application for which the imaging device is intended.

As mentioned above, the image element detectors and image element circuits could be constructed integrally on a single semiconductor substrate. Such an implemrntation is possible, but sets challenges unrelated to the present invention, relating to circuit manufacturing techniques. With suitable circuit manufacturing techniques, the invention as described herein is perfectly applicable to implementation on a single semiconductor substrate, as opposed to the dual-substrate technique described herein.

Any appropriate semiconductor materials can be used for the substrates. For example, silicon may be used for the detector substrate and for the image circuit substrate. Other semiconductor materials could be used. For example, for the detector substrate, the material could be selected from: CdZnTe, CdTe, $HgI_2$, InSb, GaAs, Ge, TIBr, Si and PbI.

By way of example, for a detector substrate material of CdZnTe the continuous electrode 36 is typically held at a voltage in the range of −100V to −600V relative to a reference voltage, whilst for CdTe, the voltage is +/−100V to +/−600V. An electric field of approximately ±200V/mm is applied between the continuous electrode 36 and image element electrodes 38 which are held at a voltage of about −/+5V or +3V. For a silicon detector substrate an electric field of +150V/0.5 mm is applied between the continuous electrode 36 and image element electrodes 38.

When an X-ray photon is photo-absorbed in a detection zone of image element detector 19 an electric charge is created, (or charged particle or gamma-ray is incident or absorbed for other embodiments) an electric pulse flows from image element detector 19 via the bum-bonds 34 to corresponding image element circuitry 20.

FIG. 2 also shows an optional guard ring area 48 integral with the detector substrate 30.

The guard ring area 48 generally surrounds all the image elements 18, and may comprise several guard rings 50. The guard rings 50 are made from a conductive material, preferably the same material as used for image element location electrodes 38 in order for the guard rings to be fabricated at the same time as the image element electrodes 38. The guard ring area 48, defined by guard rings 50, reduces charge injection due to crystal defects at the edge of the detector substrate 30 by reducing the localised increase in field strength at the edge for the detector substrate 30 material. The guard ring also helps to maintain a uniform electric field inside the detector substrate 30.

Continuous electrode 36 extends into the guard ring area 48 and also applies a bias voltage in the guard ring area 48. This forms a further detection zone hereinafter referred to as radiation detection cell 57, between the guard ring 48/50 and the continuous electrode 36. The guard ring 48/50 is exposed to radiation when the imaging device is irradiated, as well as the image element detectors 19.

Figure 3:
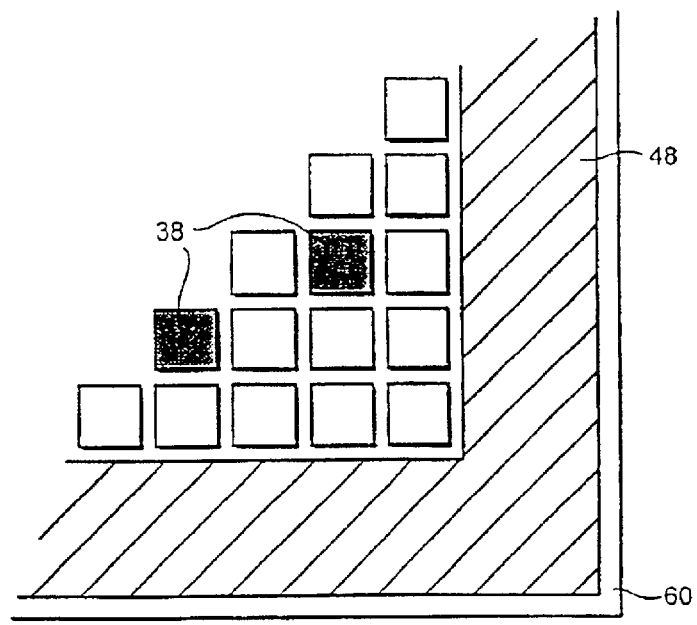
FIG. 3 is a schematic diagram of a plan view of corner of the image device of FIG. 2.

FIG. 3 shows a corner 60 of an example of a detector substrate 30 including a guard ring. Image element location electrodes 38 are disposed inside the guard ring area 48. As mentioned earlier, radiation incident on the imaging device 16 falls not only on image element location electrodes 38, but also on guard rings 50 comprising the guard ring area 48. The guard ring area 48 may comprise more than one guard ring 50 for gradually reducing the field strength towards the edge of the detector substrate 30. The guard ring 50 is coupled to output circuitry 54 via a bump-bond 52, which is directly coupled to a radiation sensor output pin on the imaging device.

Figure 4:
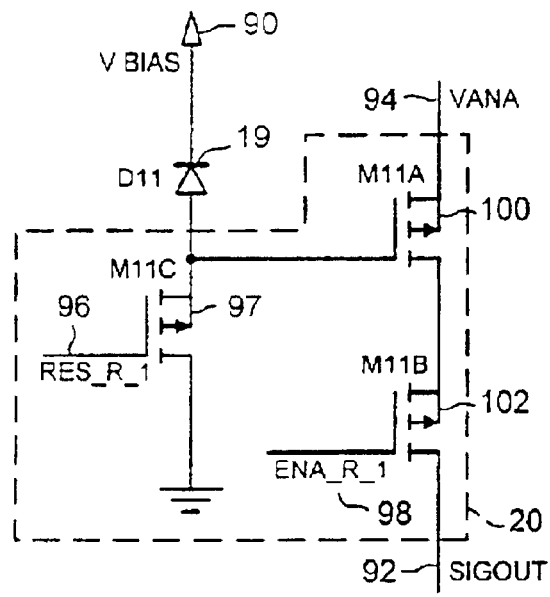
FIG. 4 is a schematic diagram of an image element circuit in accordance with an embodiment of the invention.

FIG. 4 illustrates one preferred example of an image element circuit 20 for an image element in an embodiment of an imaging device in accordance with the invention. This example uses field effect transistors (FETs) arranged as a cascode connected amplifier. VBLAS 90 is a bias voltage input across the depletion zone forming the image element detector 19 of the image element. The image element detector 19 is represented by the diode symbol D11. In the image element itself, SIGOUT 92 is an analogue signal output and VANA 94 is an analogue power supply input. RES-R-1 is a reset input and ENA-R-1 is an enable input for the image element circuit. Charge is accumulated in the gate of a transistor M11A 100 when both the RES-R-1 96 and ENA-R-1 98 inputs are low.

It will be appreciated that the use of a FET provides an example only of an embodiment of the invention in which charge accumulating capacitance is maximised using an image element charge storage device (such as a FET gate or a capacitor) that accounts for most of the input node capacitance for each pixel.

To read the pixel cell, ENA-R-1 is taken to a high state, which allows current to flow from the transistor M11A 100 through the transistor M11B 102 to SIGOUT 92. The pixel circuit is reset by taking RES-R-1 to high, whereupon after RES-R-1 has been at high for merely a few microseconds, any accumulated charge will have been removed from the gate of the transistor M11A 100. Immediately after RES-R-1 96 goes to a low level, charge can begin to accumulate at the gate of the transistor M11A 100. If no reset pulse is supplied to the reset input RES-R-1 96, then it is to be noted that a reading operation when the enable input ENA-R-1 goes high does not destroy the charge but instead merely causes a current flow directly proportional to the accumulated charge. This allows multiple readings without resetting.

Figure 5:
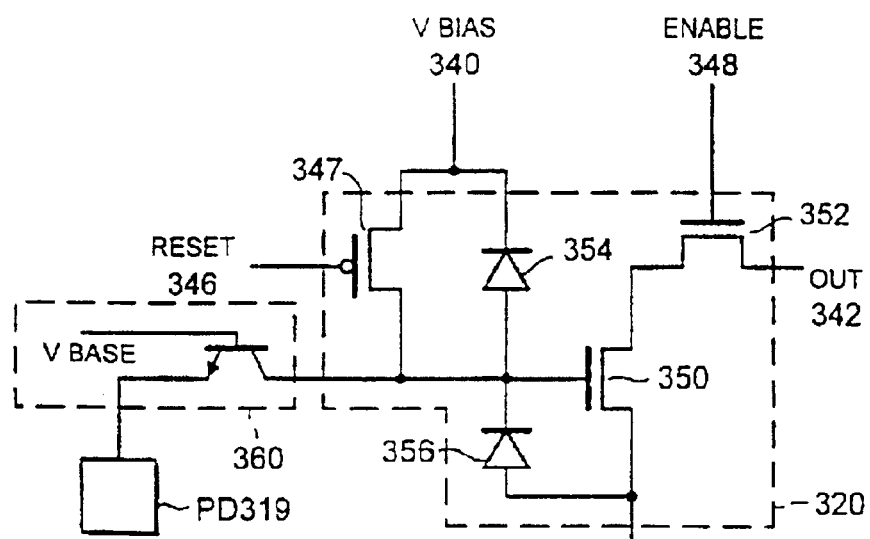
FIG. 5 is a schematic diagram of another example of an image element circuit for a further embodiment of the invention.

FIG. 5 illustrates a further example of an active image element circuit 320 for an image element in an embodiment of an imaging device in accordance with the invention. This example is similar to the example of FIG. 4. The image element detector is represented at PD 319 of the image element. In the image element circuit itself, VBLAS 340 is a voltage bias, OUT 342 is an analogue signal output, RESET 346 is a reset input connected to a reset FET 347 and ENABLE 348 is an enable input connected to an enable FET 352 for the image element circuit. Charge (electrons) is (are) accumulated in the gate of a charge storage FET 350 when the ENABLE 348 input is low and the RESET 346 input is high. To read the image element, ENABLE 348 is taken to a high state, which allows current to flow from the FET 350 through the FET 352 to OUT 342. The image element circuit is reset by taking RESET to low, whereupon after RESET 346 has been at low for merely a few microseconds, any accumulated charges will have been removed from the gate of the FET 350. Immediately after RESET 346 goes to a high level, charge can begin to accumulate at the gate of the PET 350. If no reset pulse is supplied to the reset input RESET 346, then it is to be noted that a reading operation when the enable input ENABLE goes high does not destroy the charge but instead merely causes a currently flow directly proportional to the accumulated charge. It will therefore be seen that the operation of the circuit of FIG. 5 is similar to that of FIG. 4. In addition, the circuit of FIG. 5 includes diodes 354 and 356 which act as overload protection circuitry for the image element circuit. The diodes provide protection both against static electricity which might damage the FETs and against FET overload. If the FET gate 350 accumulates more than a predetermined charge threshold (e.g. corresponding to 5 volts, which is the voltage bias), then current will start to flow through the diode 356 towards the ground, thus protecting the FET 350. This will protect image elements which, for example, receive a full radiation does outside the perimeter of an object to be imaged. Preferably, the two FETs 350 and 352 are implemented as a cascade amplifier stage. In this configuration, the two FETs 350 and 352 provide impedance-up conversion without increasing the noise accordingly. Consequently, the noise level from each pixel circuit described in the current embodiment is only about 500 e while the pixel circuit retains very small size (as small as 10–20 μm pixel size), very large dynamic range of about 50,000,000 e and individual addressability.

FIG. 5 also illustrates an optional bipolar transistor 360, which may be omitted.

In accordance with exemplary embodiments of the invention, bias 110 is supplied via the interface 22 with control electronics 24 to imaging device 16 to form bias voltage VBIAS 90 and VBIAS 340 described with reference to respective examples of the image elements 18 illustrated in FIGS. 4 and 5. Optionally, the bias 110 may be supplied directly from a power supply or other suitable module. The exemplary embodiments will be described with reference to the monitoring of bias current. However, for a power supply having a non-constant voltage, voltage may be monitored.

Figure 6:
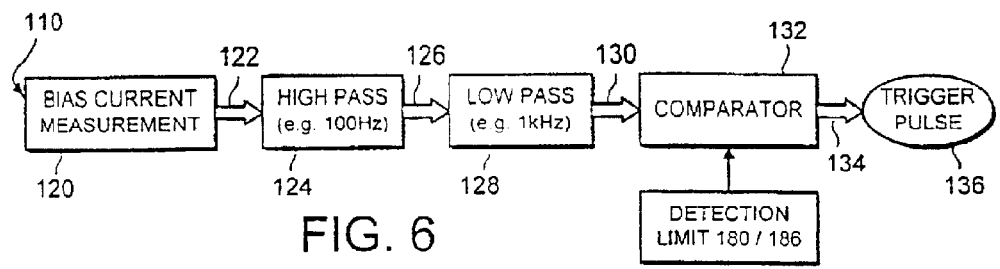
FIG. 6 is a block diagram of differential (edge) detection circuitry in accordance with a first embodiment of the invention.

Referring now to FIG. 6, there is schematically illustrated circuitry in accordance with a first embodiment of the invention for providing a trigger signal for the imaging system 10, in particular the control electronics 24 described with reference to FIG. 1. The circuitry illustrated in FIG. 6 is differential or edge detection circuitry. The bias current applied by bias 110 to the continuous electrode 36 is measured by bias current measurement unit 120. A bias current signal 122 corresponding to the measured bias current is output from bias current measurement unit 120 and input to a differentiator (high pass filter) 124. The high pass filter 124 acts to differentiate the bias current signal 122. In the illustrated embodiment, high pass filter 124 has a cut-off frequency of 100 Hz, but it will be readily apparent to the ordinarily skilled person that the cut-off frequency need not be 100 Hz but any suitable frequency capable of providing a suitable differentiation of expected or anticipated forms of bias current signal 122. For example, a suitable high pass cut-off frequency may be in the range 10–200 Hz.

A differentiated bias current signal 126 is output from high pass filter 124, and coupled to low pass filter (integrator) 128. In the illustrated embodiment, low pass filter 124 has a cut-off frequency of 1 kHz but the cut-off frequency may be any suitable frequency providing a suitable low pass filtering function for expected or anticipated ranges of differential bias current signals 126. For example, a suitable low pass cut-off frequency may be in the range 500 Hz–2 kHz.

Low pass filter (integrator 128) couples an integrated signal 130 to comparator 132 which compares integrated signal 130 with one or more threshold values. Responsive to integrated signal 130 transgressing a threshold value, comparator 132 outputs a trigger signal 134 which initiates generation of a trigger pulse 136 for the imaging system.

Figure 7:
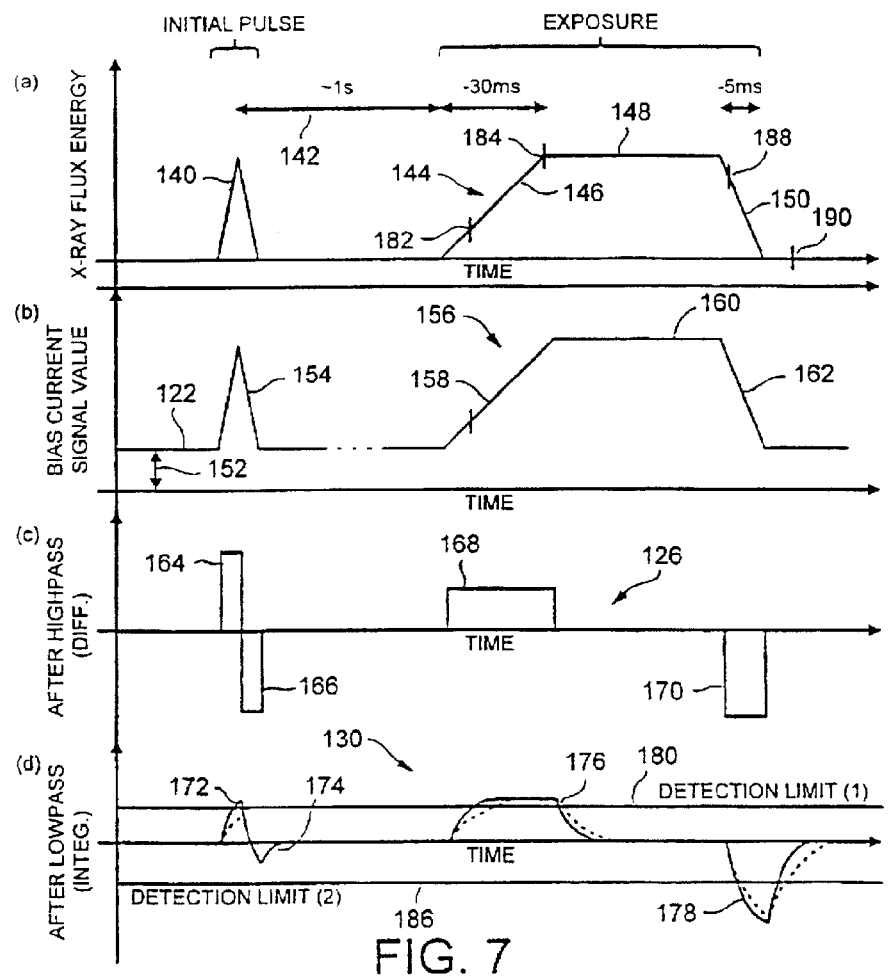
FIG. 7 illustrates the signals obtained at various points on the circuitry illustrated in FIG. 6.

An example of the variation over time of the X-ray flux energy or intensity of a typical X-ray source for medical/dental imaging during an imaging or exposure sequence is illustrated in FIG. 7(*a*). The X-ray intensity illustrated in FIG. 7(*a*) comprises an initial pulse 140 which is typically due to an impulse response or spikes from the X-ray power supply and/or pre-heating of the X-ray tube filament when the X-ray source is activated or turn on to initiated an exposure.

Initial pulse 140 may be a predetermined time period 142 (e.g. 1 second) in advance of an X-ray exposure 144, in which case it may be utilised to initiate a start of exposure trigger the predetermined time interval 142 later. However, such a trigger would not be reliable since it may vary with age, use or temperature, for example, of the X-ray source.

The X-ray exposure profile 144 starts with a slowly increasing intensity having a slope 146, and which typically lasts for about 5–50 milliseconds as illustrated. The slow increase in X-ray intensity is typically due to the gradual heating of the X-ray tubes and/or slow build-up of the X-ray source power supply voltage. Optionally, or additionally, it may be due to positive control of the X-ray source power supply to increase the lifetime of the X-ray source (tube filament). The X-ray intensity flattens out to plateau 148, and finally rapidly decreases with a large slope 150 at the end of the exposure profile 144, for example over about 5 milliseconds as illustrated.

Generally, the causes of slow rise time 146 do not occur at the end of the exposure, and thus the X-ray intensity falls off rapidly.

FIG. 7(*b*) schematically illustrates the bias signal 122 as measured by bias current measurement unit 120 for the X-ray intensity profile illustrated in FIG. 7(*a*). Bias current signal 122 has a minimum level 152 corresponding to an image device "dark" or "quiescent" current. Such a "dark" or "quiescent" current is the current flowing through the image detector elements 19 due to the bias voltage applied thereto in conditions of no- or non-exposure levels of X-ray illumination. Such "dark" or "quiescent" currents provide an offset in the measured bias current signal profile 122. The bias current may vary due to temperature variations, although such variation is typically slow.

The bias current signal profile 122 comprises an initial pulse 154 and envelope 156 having rising edge 158, plateau 160 and falling edge 162, corresponding to the X-ray intensity profile illustrated in FIG. 7(*a*). Changes in the bias current occur with changes in X-ray intensity incident on the imaging device 16, and are due to charge pairs generated in the detection zone 19 of the detector substrate in response to incident radiation migrating to respective electrodes 36,38. The greater the intensity of X-rays the greater the number of charged pairs created and thus the greater the measured bias current, and vice versa.

The signal 126 resulting from differentiating bias current signal 122 is illustrated in FIG. 7(*c*). Positive and negative square pulses 164 and 166 respectively correspond to the rising (positive) gradient and falling (negative) gradient edges of initial bias current signal pulse 154. Positive square pulse 168 corresponds to rising edge 158 to the bias current signal profile 122, and negative square pulse 120 corresponds to the falling edge 162. The effect of low pass filtering signal 126 is illustrated in FIG. 7(*d*).

Although there are pulses (172, 174, 176, 178) in signal 130 corresponding to the pulses (164, 166, 168, 170) in signal 126, the are modified such that the pulse 174 corresponding to pulse 166 of signal 126 is a lower amplitude than pulse 178 corresponding to pulse 170 of signal 126. By appropriate adjustment of the low pass filter (reducing the cut-off frequency) pulse 172 may be attenuated (shown in broken lines) with respect to pulse 176). Such modification would also change the shape of pulses 176 and 178 (broken line) but they would still achieve at least substantially the same amplitude as for an unmodified low pass filter 128.

For a modified low pass filter signal 130 transgresses detection limit (1) 180, which corresponds to a first threshold value for comparator 132, by pulse 176 only. The crossing of threshold 180 by respective rising and falling edges of pulse 176 corresponds to points 182 and 184 respectively on the X-ray exposure profile 144, and to corresponding threshold values for the bias current signal illustrated in FIG. 7(b). Thus, respective transgressions of value 180 may be utilised to initiate a start of exposure trigger for use by the imaging system 10, depending upon whether the start of exposure is determined to be just as the X-ray exposure begins, point 182, or where the X-ray intensity has reached a substantially constant level, point 184. Comparator 132 may comprise discrete logic circuitry hardwired to respond to one or other transgressions of threshold 180 to initiate trigger pulse unit 136 to produce a start of exposure trigger signal for control electronics 24 of the imaging system.

As is also illustrated in FIG. 7(d) negative going pulse 178 transgresses a second threshold level 186 (detection limit (2)). Pulse 178 crosses threshold 186 on both falling and rising edges, corresponding to point 188 and 190, respectively in the X-ray intensity profile illustrated in FIG. 7(a). Typically, comparator 132 is configured to respond to transgressions of threshold 186 by the falling edge (first transgression) of pulse 178 to initiate trigger pulse unit 136 lo produce an end of exposure trigger signal for the imaging system, indicating that the X-ray exposure is completed, and image readout should begin.

Comparator 132 need not be comprised of discrete logic circuitry but may comprise a suitably configured programmable logic array or a suitably programmed processing unit. Indeed, all the modules post bias current measurement illustrated in FIG. 6 may be implemented in a suitably programmed processing unit such as a field programmable gate array, or even a general purpose processor. However, for operation, e.g data or clock frequencies greater than 100 kHz, an optimised Application Specific Integrated Circuit would be required.

Optionally, the low pass filter is unmodified and signal 130 is represented by the unbroken lines of FIG. 7(d). In such an embodiment, either comparator 132 is configured to discard transgressions of threshold 180 by pulse 172, or optionally, comparator 132 is configured to respond to transgressions of threshold 186 only, thereby initiating only an end of exposure trigger signal. This may be achieved by setting only a single threshold level 186 (detection limit (2)). Any desired start of exposure trigger for the imaging system would then need to be provided by some other means.

Figure 8:
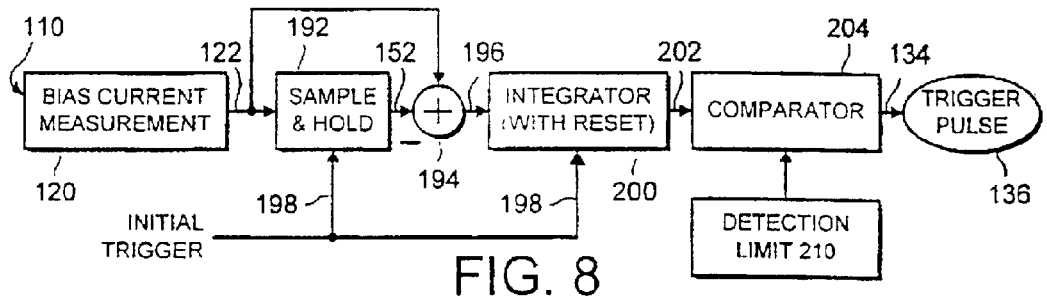
FIG. 8 is a block diagram of a dose detection trigger circuitry in accordance with a second embodiment of the invention.

Circuitry in accordance with a second embodiment of the invention is illustrated in FIG. 8. The second embodiment may be termed a dose detection trigger circuit, since it provides a trigger pulse depending on the accumulated radiation or radiation dose received by the imaging device 16.

Bias current measurement unit 120 and bias current signal 122 operate as described with reference to the first embodiment illustrated in FIG. 6. Similarly, the X-ray intensity profile and bias current signal profile 122 respectively illustrated in FIGS. 9(a) and 9(b) are as described with reference to FIGS. 7(a) and 7(b) above.

Bias current signal 122 is input to resettable sample and hold unit 192, and to subtraction circuitry 194. The output 152 of sample and hold unit 192 is input to subtraction circuitry 194, and is subtracted from bias current signal 122. The sample and hold unit 192 also receives an initial trigger signal 198 which resets unit 192 and may be utilised to reset unit 192 just prior to an X-ray exposure in order to store the "dark" or "quiescent" current value 152 just prior to the X-ray exposure. The initial trigger signal may correspond to an X-ray trigger originating from the X-ray source to indicate the start of an exposure or may occur periodically outside of an X-ray exposure window.

A dark current corrected signal 196 is input to a resettable integrator 200, which is reset on receipt of initial trigger signal 198, and provides an integrated signal 202 to comparator 204. Comparator 204 outputs trigger signal 136 for the integrated signal 202 transgressing a threshold value for the comparator. The trigger signal 134 is coupled to trigger pulse unit 136 which provides a trigger pulse to the control electronics 20 for the imaging system 10.

Figure 9:
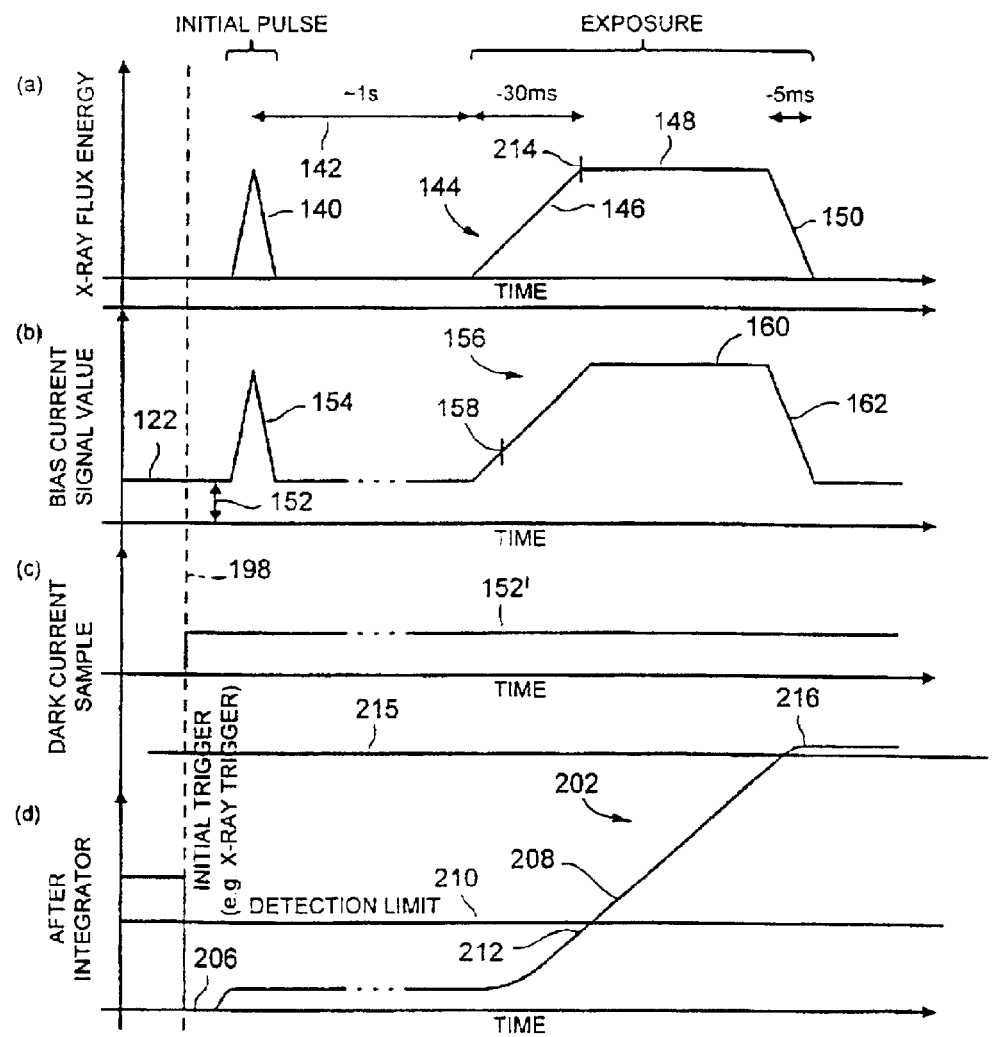
FIG. 9 illustrates signals obtained at various points in the circuitry illustrated in FIG. 8.

As mentioned above, FIGS. 9(a) and 9(b) illustrate a typical X-ray intensity profile and bias current signal 122 as described with reference to FIGS. 7(a) and 7(b). FIG. 9(c) illustrates a sample, 152', of the dark current 152 stored in response to an initial trigger 198 shown in broken line on FIG. 9. The initial trigger 198 also resets integrator 200 as illustrated by reference to 206 in FIG. 9(d). The signal 202 output from integrator 200 has a profile as illustrated. Initially, the profile ramps up, 208, corresponding to initial X-ray pulse 140, and flattens-out until exposure pulse 144 during which signal 202 increases until the X-ray intensity drops off, 150. Comparator 204 includes a threshold value 210 corresponding to the detection limit illustrated in FIG. 9(d). For signal 202 transgression threshold 210 a trigger signal 134 is output from comparator 204 to the trigger pulse unit 136. The detection limit is set at a value at least greater than the signal 202 value due to pulse 140, but thereafter may be set at any suitable level to initiate a trigger pulse imaging system 10. A suitable detection limit 210 would result in signal 202 transgressing a threshold at point 212, which corresponds to the start of constant X-ray intensity illumination, labelled 214 in FIG. 9(a), and to a corresponding threshold for the bias current signal illustrated in FIG. 9(b). Such a trigger would be a start of exposure trigger. An end of exposure trigger may be automatically generated by the imaging system, a predetermined time period after the start of exposure trigger signal. Optionally, plateau 216 may be identified by the system in order to initiate an end of exposure trigger, or a second threshold 215 may be set for the comparator 204, the transgression of which initiates an end of exposure trigger pulse.

Figure 10:
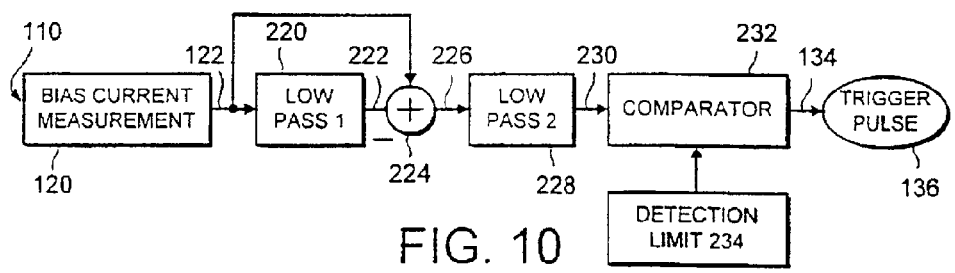
FIG. 10 is a block diagram of further dose detection trigger circuitry in accordance with a third embodiment of the invention.
Figure 11:
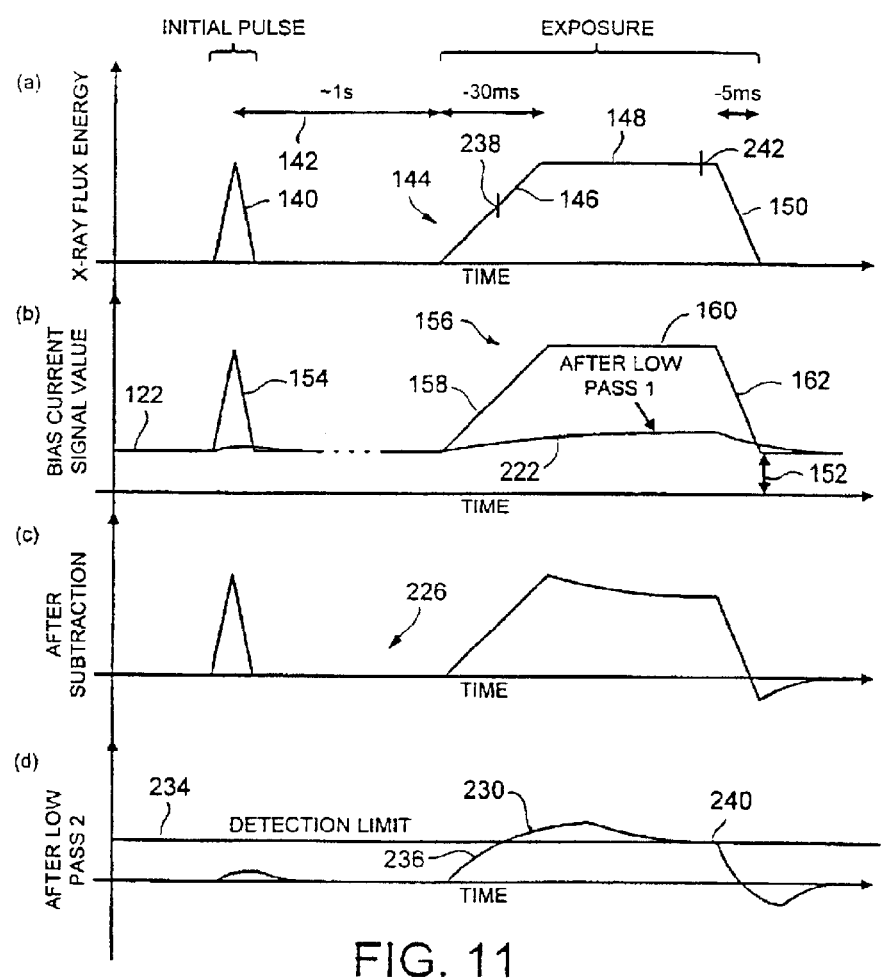
FIG. 11 illustrates signals obtained at various points in the circuitry illustrated in FIG. 10.

A third embodiment of the invention comprises a second dose detection trigger circuit as illustrated in FIG. 10. A second dose detection trigger circuit replaces the sample and hold unit 192 and integrator 200 of the circuitry illustrated in FIG. 8, with simple low pass filters 220 and 228, respectively. Utilising such a configuration obviates the need for an initial trigger and thereby reduces the complexity of the imaging system 10 control circuitry 24.

As illustrated in FIG. 10, bias current signal 122 is input to low pass filter 220, preferably having a cut-off frequency in the range 10–200 Hz for example, and to subtraction circuitry 224. Subtraction circuitry 224 subtracts the low pass filtered bias current signal 222 from the raw bias current signal 122 to produce signal 226 which is corrected for the dark current. This is due to the fact that since the dark current slowly varies over time (e.g. due to changes in temperature), the measured bias current profile after low pass filtering is substantially similar to its unfiltered profile. The profile of signal 226 is illustrated in FIG. 9(c).

Signal 226 is input to the second low pass filter 228, preferably having a cut-off frequency in the range 10–200 Hz for example, resulting in a signal 230 having a profile as illustrated in FIG. 9(d). Comparator 232 receives signal 230 from low pass filter 228, and compares it with a threshold value 234 (detection limit). As illustrated in FIG. 9(d), signal 230 upwardly transgresses threshold 234 at point 236 corresponding to point 238 on the X-ray intensity profile 144. Thus, the comparator can output a trigger signal to trigger pulse unit 136 to initiate a start of exposure trigger.

Comparator 232 may also output a trigger signal corresponding to a downward transgression of threshold 234 at point 240 corresponding to point 242 on the X-ray intensity profile 144, to initiate an exposure trigger signal.

By passing signal 226 through a second low pass filter 228, the magnitude of signal corresponding to the initial pulse 140 is greatly reduced, relative to the signal corresponding to the X-ray exposure profile 144. Therefore, the likelihood of false triggering due to the initial pulse 140 is reduced.

Figure 12:
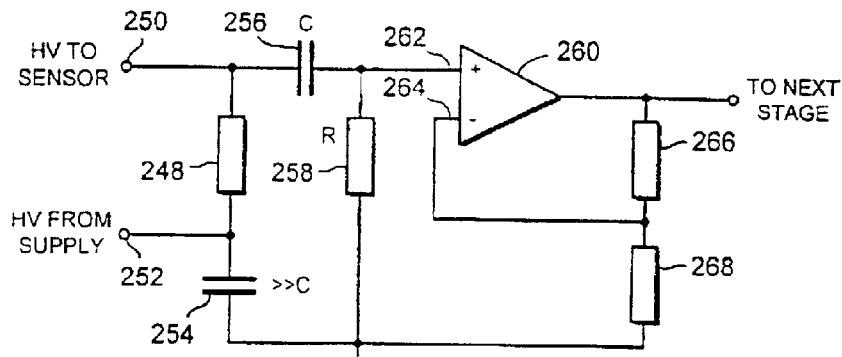
FIG. 12 is a schematic circuit diagram of a bias current measurement suitable for embodiments of the present invention.

An example of bias current measurement circuitry suitable for embodiments of the invention, in particular edge detection circuitry, will now be described with reference to FIG. 12. The high voltage power supply and electronic circuit of the imaging system are coupled to a common reference potential, for example ground. Thus, bias measurement is undertaken by coupling a resistor 248 across the high voltage node 250 for the image device 16 and high voltage node 252 from the power supply. Optionally, it is possible to measure bias current directly from ground if the power supply is floating. Such optional measurement configuration advantageously allows DC coupling and implementation of a compensation measurement method.

The power supply node end of resistor 248 is coupled to the reference potential (ground) via capacitor 254. The image device node end of resistor 248 is coupled to the positive input 262 of operational amplifier (op-amp) 260 via a capacitor 256 having a value C. A resistor having a value R, 258, is coupled between the positive input 262 and the reference potential. The time constant of the RC combination of capacitor 256 and resistor 258 is selected to be low relative to the time constant of the subsequent stages of the circuitry, for example to the time constant providing the cut-off frequency of the high-pass filter stage of the edge detection circuitry. The value of capacitor 254 is much greater than the value of the capacitor 256. The value of the current sense resistor 248 is selected to provide sufficient voltage between nodes 250 and 252 to provide a reliable signal for measurement, yet without unacceptably affecting the operation of the image device detectors, and being sufficiently less than the value R of resistor 258 not to influence the time constant of the bias current measurement circuitry.

The output of op amp 260 is coupled to a resistor chain comprising resistors 266 and 268, the centre of which is fed back to the negative input 264 of the op amp 260 to provide a suitable feedback signal. The output is then coupled to the next stage of the circuitry.

Figure 13:
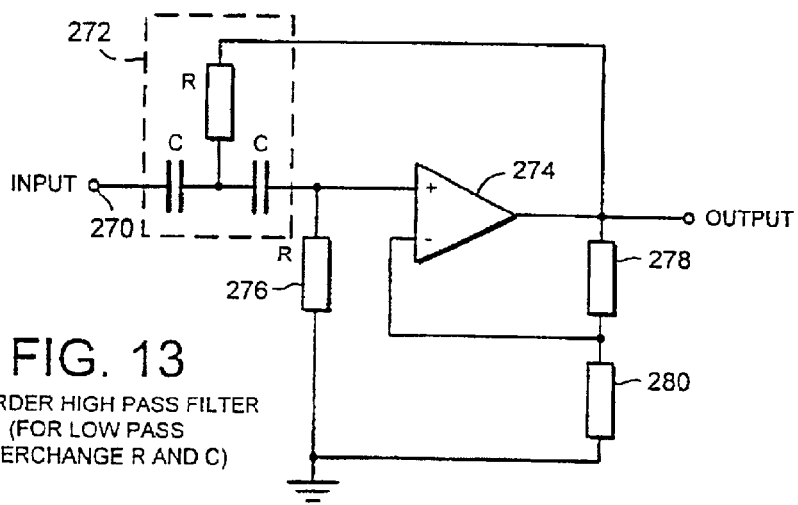
FIG. 13 is a schematic circuit diagram of a second order high pass filter suitable for a differentiator in accordance with embodiments of the invention.

FIG. 13 illustrates a second order high pass filter suitable for providing a differentiator for the edge detection circuitry described above. Although the present description refers to a second order filter, a first order filter or higher order filters may be used. Input 270 receives bias current signal 122 from the bias current measurement unit 120, and is fed into a C-R-C network 272. The output of the C-R-C network 272 is input to the positive input of the operational amplifier (op-amp) 274 which is also coupled to reference potential (ground) via a resistor 276. The output of the op-amp 274 is coupled to the reference potential (ground) via a resistor network 278,280, centre tapped to provide a feedback to the negative input of the op amp 274. The output of the op-amp is also fed back to the network 272.

For a low pass filter, the capacitors are interchanged with the resistors.

The high and low pass filters are preferably implemented having critically damped characteristics. However, by changing the op amp gain, more complex filter characteristics may be achieved. For example, for critical damping the gains equal 1.0. For a Bessel function the gain equals 1.268 and for a 3 dB Tscbebyscheff filter, the gain equals 2.234, for example.

Figure 14:
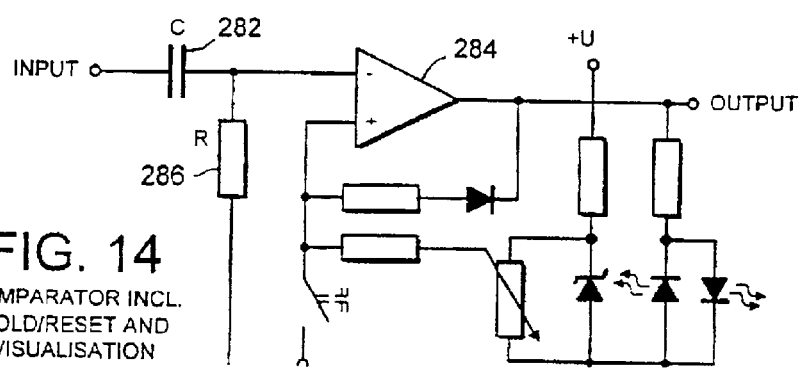
FIG. 14 is a schematic circuit diagram of a comparator suitable for embodiments of the present invention.

An example of a comparator circuit suitable for embodiments of the invention is illustrated in FIG. 14. An input signal is coupled via AC coupling capacitor 282 to the negative input of operational amplifier(op-amp) 284. The negative input is also coupled to reference potential (ground) by resistor 286. AC coupling is advantageous to reject any DC offset voltage derived from the preceding operational amplifier stage circuitry due to the operational amplifier characteristics. Since the particular implementation details of the comparator circuitry are not relevant to the instant invention, and the skilled person will be aware of and understand the various circuit configurations available for forming a comparator, no further description will be provided.

FIGS. 15 to 24 of the drawings illustrate oscilloscope plots of signals obtained from the low pass filter 128 of the differential edge detection circuitry, i.e. signal 130 as illustrated in FIG. 7(d). However, due to the electrical circuit configuration used in conducting the experiments, the oscilloscope traces illustrated in FIGS. 15 to 24 are inverted with respect to the signal 130 illustrated in FIG. 7(d).

The results are obtained using edge detection circuitry comprising bias current measurement unit, high and low pass filters and comparators substantially as described with reference to FIGS. 12, 13 and 14.

The results are achieved using a Planmeca dental X-ray source having the recommended 2 mm Al filtration and 30 cm focal spot to imaging device 16 distance. The X-ray source was set to an 8 milliamp current, and 63 kV voltage and of 10 millisecond duration. Measurements were made with 200/2000 Hertz and 100/1000 Hertz high passflow pass filter settings. For each filter combination the comparator was kept constant at maximum sensitivity in order to inhibit any unwanted triggering. The imaging device received the clock signal, and the sensor and electronics were optically and electrically unshielded. The test results were achieved firstly without an object, then with a dental phantom, then with 4 mm and subsequently with 12 mm Al targets.

Figure 15:
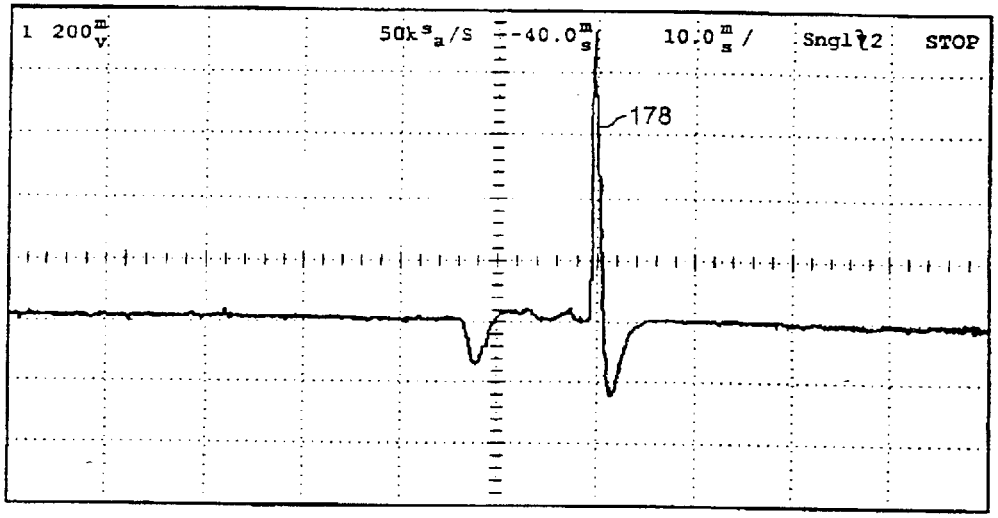
FIGS. 15–24 illustrate oscilloscope plots of an integrated signal for various configurations of circuitry substantially in accordance with the first embodiment of the invention.
Figure 16:
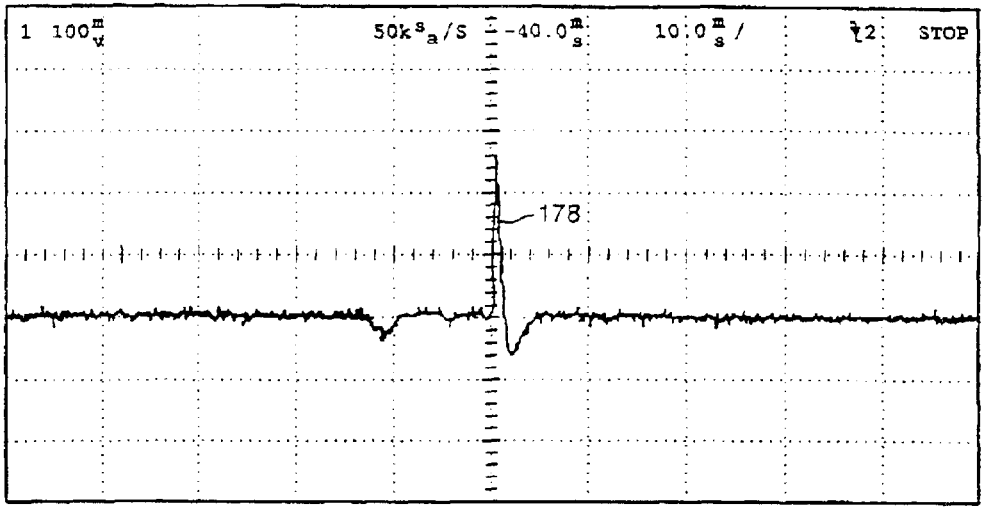
Figure 17:
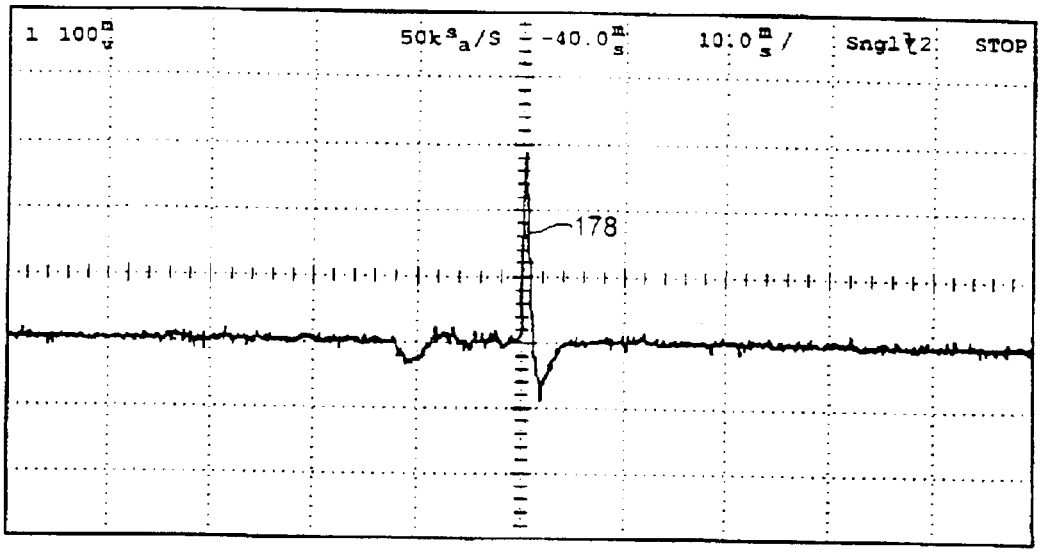
Figure 18:
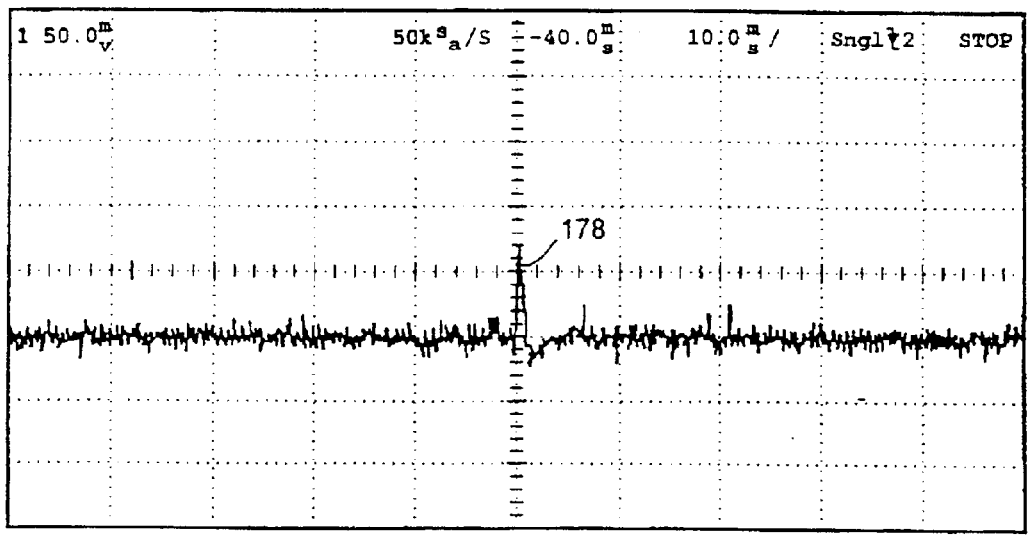
Figure 19:
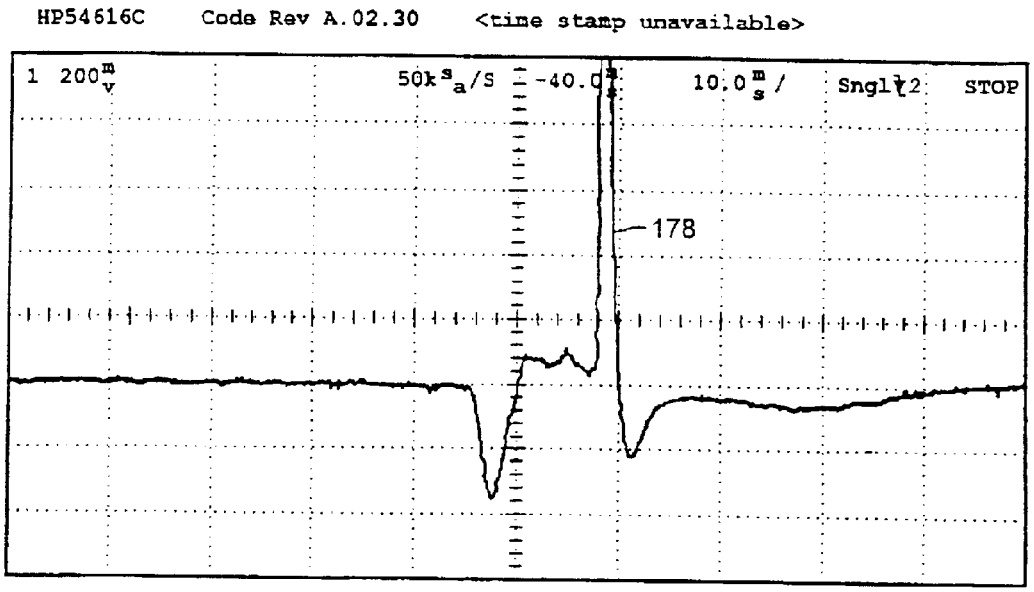
Figure 20:
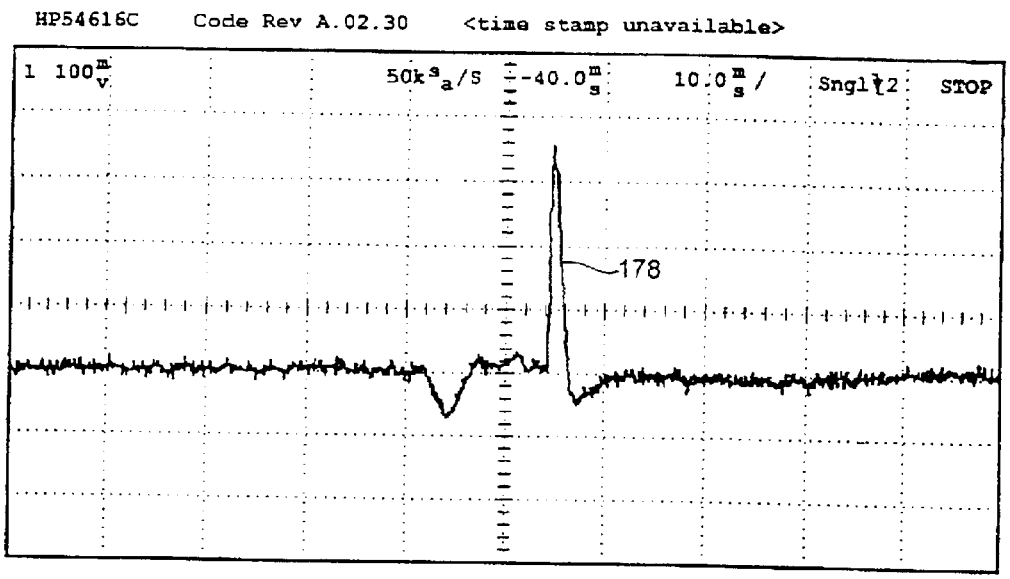
Figure 21:
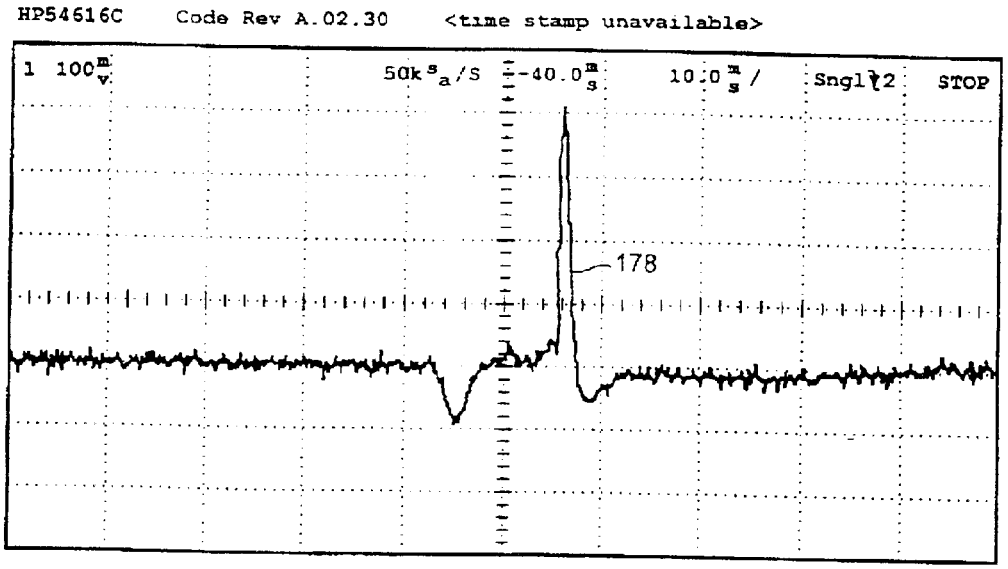
Figure 22:
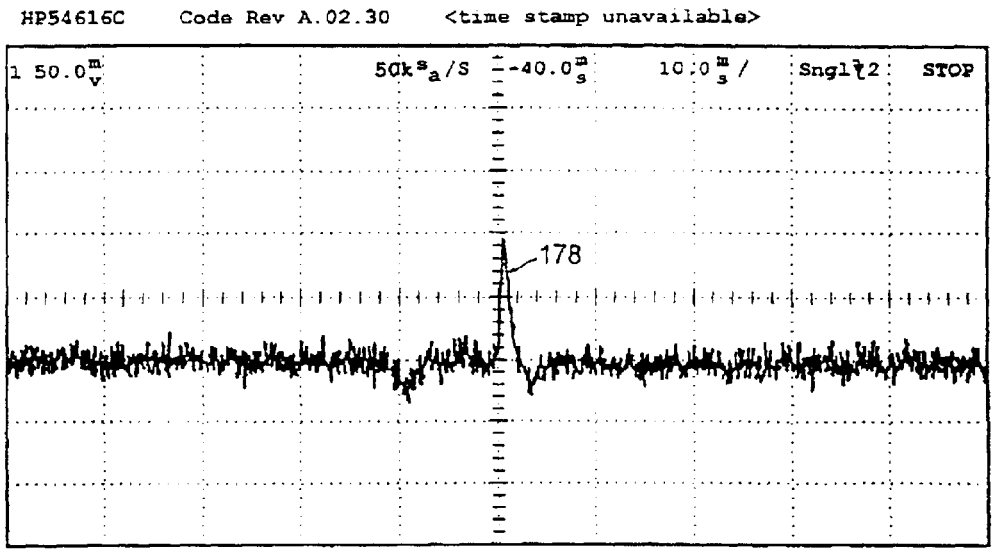

For the plots illustrated in FIGS. 15 to 24, the imaging device was in standby mode and no readout or reset was performed. The signal corresponding to pulse 178 of FIG. 7(d) is also marked 178 in FIGS. 15 to 24. As expected, the amplitude of the pulses 178 is higher for the 100/1000 Hertz configuration, compared to the 200/2000 Hertz configuration. This result should be expected from the function of a high pass filter. FIG. 15 has no object, and the oscilloscope trace clearly shows the rising and falling flank corresponding to the bias current. As the object absorbs and increases only the pulse corresponding to the falling edge of the bias current exceeds the noise flaw. This progression is shown in FIGS. 15 and 19 for no target and 200/2000 Hertz and 100/1000 Hertz filter configurations respectively. FIGS. 16 and 20 for the dental phantom target indicate that there has been a reduction in the flanks of the bias current, and FIGS. 17 and 21 and FIGS. 18 and 22 respectively for a 4 mm and 12 mm thick Al target show continued gradual reduction in the bias current flanks as the absorption level of the target increases.

Without any object, the triggering occurs before the falling edge. This is due to the sensitive adjustment of the comparator register an overshoot from the rising edge as well as a ripple of the X-ray intensity. Having an adequately selectable readout sequence should ameliorate this problem.

Figure 23:
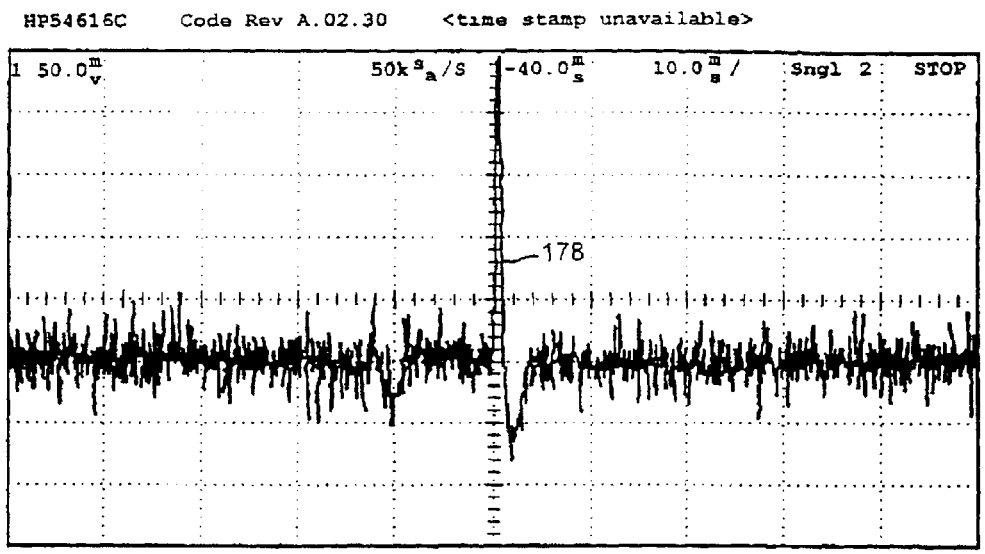
Figure 24:
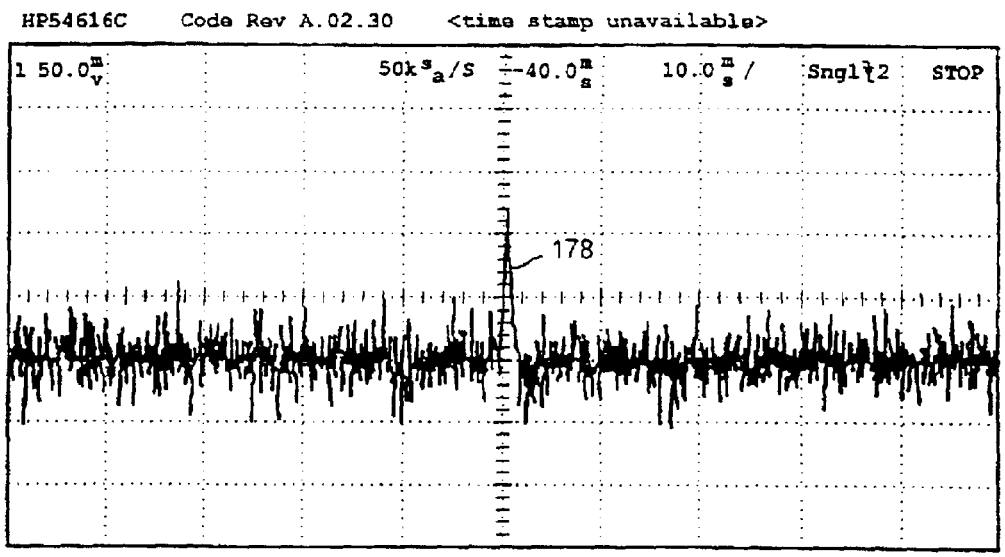

FIGS. 23 and 25 show the oscilloscope trace obtained when the imaging device is in operation. Continuous readout/reset was performed on the imaging device. Due to relatively simple filtering the reset frequency of the imaging device was about 30 kHz and became visible forcing a higher comparator voltage, thereby reducing sensitivity. In the 200/2000 Hertz configuration, the X-ray exposure cannot be detected with a 12 mm Al target but could be detected easily with a 4 mm Al target. In the 100/1000 Hertz configuration, the X-ray exposure could still be detected with the 12 mm Al target, with respect to traces illustrated in FIGS. 23 and 24.

In view of the foregoing description it will be evident to a person skilled in the art that various modifications may be made within the scope of the invention. For example, the system could be used for non-destructive testing and analysis, as well as in medical imaging. Additionally, the high pass filter cut-off frequency may be determined by the following relationship, $f_{hpf}=2/t_{X\text{-ray pulse duration}}$, and low pass cut-off frequency by $f_{lpf}=2/t_{X\text{-ray pulse rise/fall time}}$. The bias measurement unit, high and low pass filters and comparator unit need not be as specifically described above. In particular, all the elements after the bias measurement circuitry illustrated in respective FIGS. 6, 8 and 10 may be implemented in a Field Programmable gate Array or general purpose processor. However, for operation, e.g. data or clock rates greater than 100 kHz, an optimised Application Specific Integrated Circuit should be used.

Although the X-ray source referred to in the foregoing description provides an initial X-ray pulse, the present invention is not limited to use with such X-ray sources, but to any form of X-ray source output and high energy radiation sources in general.

The scope of the present disclosure includes any novel feature or combination of features disclosed therein either explicitly or implicitly or any generalisation thereof irrespective of whether or not it relates to the claimed invention or emitigates any or all of the problems addressed by the present invention. The application hereby gives notice that new claims may be formulated to such features during the prosecution of this application or of any such further application derived therefrom. In particular, with reference to the appended claims, features from dependent claims may be combined with those of the independent claims in any appropriate manner and not merely in the specific combinations enumerated in the claims.

What is claimed is:

1. A semiconductor radiation imaging assembly, comprising:
   a semiconductor imaging device including at least one high energy direct conversion image element detector;
   said semiconductor imaging device comprising a semiconductor substrate supporting a first and second conductive layer on respective first and second surfaces, said second conductive layer comprising an image element electrode and said first and second conductive layers at least partially opposing each other for applying a bias therebetween to define a radiation detection zone for said image element detector; and
   bias signal monitoring means for monitoring a bias signal applied to said first conductive layer for determining radiation incident on said image element detector.

2. An imaging assembly according to claim 1, wherein said first conductive layer comprises a substantially continuous layer across said first substrate surface, and said second conductive layer comprises a plurality of image element electrodes for defining respective radiation detection zones for a plurality of image element detectors.

3. An imaging assembly according to claim 1 wherein said bias signal monitoring means is adapted to provide a trigger signal for said bias signal fulfilling a predetermined criterion.

4. An imaging assembly according to claim 3, wherein said trigger signal is initiated in response to a transgression of a threshold value for said bias signal indicative of a start of a radiation exposure or end of a radiation exposure.

5. An imaging assembly according to claim 4, wherein said trigger signal comprises a begin exposure trigger signal for said threshold value indicative of said start of radiation exposure.

6. An imaging assembly according to claim 5, wherein said trigger signal is initiated in response to said bias signal upwardly transgressing said threshold value.

7. An imaging assembly according to claim 4, wherein said trigger signal comprises an exposure trigger for said threshold value indicative of said end of radiation exposure.

8. An imaging assembly according to claim 7, wherein said trigger signal is initiated in response to said bias signal downwardly transgressing said threshold value.

9. An imaging assembly according to claim 1, wherein said bias signal monitoring means is adapted to determine a rate of change for said bias signal.

10. An imaging assembly according to claim 9, wherein said bias signal monitoring means is adapted to discriminate between more than one rate of change of said bias signal.

11. An imaging assembly according to claim 1, said bias signal monitoring means comprising:
    a differentiator for differentiating a signal representative of said bias signal;
    a low pass filter for low pass filtering said differentiated signal; and
    a comparator for comparing said low pass filtered signal with a threshold value.

12. An imaging assembly according to claim 11, wherein said differentiator comprises a high pass filter.

13. An imaging assembly according to claim 1, wherein said bias signal monitoring means is adapted to determine accumulated bias signal values representative of aggregate radiation incident on said image element detector.

14. An imaging assembly according to claim 13, wherein said bias signal monitoring means is responsive to said accumulated bias signal value fulfilling a predetermined criterion to initiate a trigger signal.

15. An imaging assembly according to claim 14, wherein said predetermined criterion comprises said accumulated bias signal value transgressing a first threshold value thereby providing a begin of exposure trigger signal.

16. An imaging assembly according to claim 14, wherein said predetermined criterion comprises said accumulated bias signal value transgressing a second threshold value to provide an end of exposure trigger signal.

17. An imaging assembly according to claim 16, wherein said bias signal monitoring means is adapted to subtract an image element quiescent bias signal value from a signal representative of said bias signal.

18. An imaging assembly according to claim 17, wherein said bias signal monitoring means further comprises sample and hold circuitry for recording an image element quiescent bias signal value; and subtraction means for subtracting said image element quiescent bias signal value from said signal representative of said bias signal so as to form a quiescent bias signal corrected bias signal.

19. An imaging assembly according to claim 18, wherein said sample and hold circuitry is resettable to update said recorded image element quiescent bias signal value prior to said bias signal monitoring means initiating measurement of said accumulated bias signal.

20. An imaging assembly according to claim 16, said bias signal monitoring means comprising:
an integrator for integrating a signal representative of said bias signal; and
a comparator for comparing said integrated signal with said first and/or second threshold value.

21. An imaging assembly according to claim 1, wherein said bias signal monitoring means is adapted to integrate a signal representative of said bias signal and to subtract said integrated signal from said signal representative of said bias signal so as to derive a signal representative of radiation incident on said image element detector.

22. An imaging assembly according to claim 21, wherein said bias signal monitoring means is adapted to integrate said signal representative of radiation so as to generate an integrated signal representative of radiation.

23. An imaging assembly according to claim 22, wherein said bias signal monitoring means is responsive to said integrated signal representative of radiation fulfilling a predetermined criterion to provide a trigger signal.

24. An imaging assembly according to claim 23, wherein said predetermined criterion comprises said integrated signal representative of radiation transgressing a first threshold value to provide a start of exposure trigger signal.

25. An imaging assembly according to claim 24, wherein said predetermined criterion comprises said integrated signal representative of radiation transgressing a second threshold value to provide an end of exposure trigger signal.

26. An imaging assembly according to claim 25, wherein said bias signal monitoring means comprises a comparator for comparing said integrated signal representative of radiation with said first threshold value and/or said second threshold value.

27. An imaging assembly according to claim 1, wherein said bias signal monitoring means is adapted to monitor bias signal current.

28. An imaging assembly according to claim 1, wherein said bias monitoring means is adapted to monitor bias signal voltage.

29. An imaging assembly according to claim 1, wherein said image device comprises a plurality of detector elements, and said bias monitoring means is arranged to monitor said bias signal for at least some of said image elements.

30. An imaging assembly according to claim 29, wherein said bias monitoring means is arranged to monitor said bias signal for all of said image elements.

31. An imaging assembly according to claim 1, wherein said bias signal monitoring means is integral with said imaging device.

32. A semiconductor radiation imaging system, comprising:
a semiconductor imaging assembly according to claim 1;
control electronics coupled to said imaging assembly for receiving signals, including trigger signals, therefrom;
signal storage means for storing signals coupled from said control electronics;
an image processor for processing signals coupled from said control electronics; and
a display unit for displaying images provided by said image processor.

33. An imaging system according to claim 32, wherein said control electronics are responsive to a trigger signal from said imaging assembly to initiate an image frame selection from said signals stored in said storage means.

34. A method for providing a self-triggerable semiconductor imaging assembly, the assembly comprising a semiconductor imaging assembly according to claim 1, said method comprising:
monitoring a bias signal for applying a bias to said image element detector so as to monitor radiation incident on said image element detector; and
initiating a trigger signal conditional on said bias signal fulfilling a predetermined condition.

35. A method according to claim 34, further comprising determining a change in said bias signal corresponding to a change in radiation incident on said image element detector.

36. A method according to claim 35, further comprising determining a rate of change for said bias signal.

37. A method according to claim 36, further comprising discriminating between more than one rate of change for said bias signal.

38. A method according to claim 37, in which said trigger signal comprises a start of exposure trigger signal for said rate of change indicative of a start of radiation exposure.

39. A method according to claim 36, in which said rate of change is indicative of a start of radiation exposure or end of radiation exposure.

40. A method according to claim 39, in which said trigger signal comprises an end of exposure trigger signal for said rate of change indicative of an end of radiation exposure.

41. A method according to claim 34, further comprising determining an accumulated bias signal representative of aggregate radiation incident on said image element detector.

42. A method according to claim 41, further comprising initiating a trigger signal for said accumulated bias signal fulfilling a predetermined condition.

43. A method according to claim 42, in which said predetermined condition comprises said accumulated bias signal transgressing a threshold value.

44. A method according to claim 43, further comprising initiating a start of exposure trigger signal for said accumulated bias signal transgressing a first threshold value.

45. A method according to claim 43, further comprising initiating an exposure trigger signal for said accumulated bias signal transgressing a second threshold value.

46. A method according to claim 41, further comprising:
determining an image element detector quiescent bias signal value;
subtracting said image element detector quiescent bias signal value from a signal representative of said bias signal; and
accumulating said bias signal after subtraction of said image element detector quiescent bias signal value.

47. A method according to claim 34, further comprising:

low pass filtering a signal representative of said bias signal;

subtracting said low pass filtered signal from said signal representative of said bias signal for deriving a signal representative of radiation incident on said image element detector;

low pass filtering said signal representative of radiation; and initiating a trigger signal for said low pass filtered signal representative of radiation fulfilling a predetermined condition.

48. A method according to claim 47, further comprising initiating a start of exposure trigger signal for said low pass filtered signal representative of radiation transgressing a first threshold value.

49. A method according to claim 47, further comprising initiating an exposure trigger signal for said integrated signal representative of radiation transgressing a second threshold value.

50. A method according to claim 34, wherein said step of monitoring said bias signal comprises monitoring bias signal current.

51. A method according to claim 34, wherein said step of monitoring said bias signal comprises monitoring bias signal voltage.

52. A semiconductor radiation imaging assembly, comprising:

a semiconductor imaging device including at least one high energy direct conversion image element detector;

said semiconductor imaging device comprising a semiconductor substrate supporting a first and second conductive layer on respective first and second surfaces, said second conductive layer comprising an image element electrode and said first and second conductive layers at least partially opposing each other for applying a bias therebetween to define a radiation detection zone for said image element detector; and bias monitoring means for monitoring a bias signal applied to said conductive layer, said bias monitoring means being for use in controlling readout from said radiation detection zone so as to determine radiation incident on said image element detector.

* * * * *